(12) United States Patent
Bouaboula et al.

(10) Patent No.: US 11,260,057 B2
(45) Date of Patent: Mar. 1, 2022

(54) COMBINATION COMPRISING PALBOCICLIB AND 6-(2,4-DICHLOROPHENYL)-5-[4-[(3S)-1-(3-FLUOROPROPYL)PYRROLIDIN-3-YL]OXYPHENYL]-8,9-DIHYDRO-7H-BENZO[7]ANNULENE-2-CARBOXYLIC ACID AND ITS USE FOR THE TREATMENT OF CANCER

(71) Applicant: SANOFI, Paris (FR)

(72) Inventors: Monsif Bouaboula, Paris (FR); Maysoun Shomali, Bridgewater, NJ (US); Fangxian Sun, Bridgewater, NJ (US)

(73) Assignee: SANOFI, Paris (FR)

( * ) Notice: Subject to any disclaimer, the term of this patent is extended or adjusted under 35 U.S.C. 154(b) by 42 days.

(21) Appl. No.: 16/634,089

(22) PCT Filed: Jul. 23, 2018

(86) PCT No.: PCT/EP2018/069901
§ 371 (c)(1),
(2) Date: Jan. 24, 2020

(87) PCT Pub. No.: WO2019/020559
PCT Pub. Date: Jan. 31, 2019

(65) Prior Publication Data
US 2020/0171033 A1    Jun. 4, 2020

Related U.S. Application Data

(60) Provisional application No. 62/536,121, filed on Jul. 24, 2017.

(30) Foreign Application Priority Data

Jul. 25, 2017 (EP) .................. 17305998

(51) Int. Cl.
 *A61K 31/519* (2006.01)
 *A61K 31/40* (2006.01)

(52) U.S. Cl.
CPC ............ *A61K 31/519* (2013.01); *A61K 31/40* (2013.01)

(58) Field of Classification Search
CPC .................. A61K 31/40; A61K 31/519
See application file for complete search history.

(56) References Cited

U.S. PATENT DOCUMENTS

| | | | |
|---|---|---|---|
| 6,495,607 B2 | 12/2002 | Bohlmann et al. |
| 7,429,681 B2 | 9/2008 | Pinney et al. |
| 7,612,114 B2 | 11/2009 | Hamaoka et al. |
| 7,799,824 B2 | 9/2010 | Lagu et al. |
| 8,299,112 B2 | 10/2012 | Smith et al. |
| 9,309,211 B2 | 4/2016 | Xiao et al. |
| 9,540,361 B2 | 1/2017 | Dijcks et al. |
| 9,714,221 B1 | 7/2017 | Bouaboula et al. |
| 9,845,291 B2 | 12/2017 | Liang et al. |
| 10,570,090 B2 | 2/2020 | Bouaboula et al. |
| 10,966,963 B2 | 4/2021 | Labadie et al. |
| 2012/0130219 A1 | 5/2012 | Pinney et al. |
| 2013/0252890 A1 | 9/2013 | Wintermantel et al. |
| 2015/0080438 A1 | 3/2015 | Wintermantel et al. |
| 2018/0153828 A1 | 6/2018 | Garner et al. |
| 2020/0155521 A1* | 5/2020 | Schwartz ............ A61K 31/502 |
| 2020/0361918 A1 | 11/2020 | Bouaboula et al. |
| 2020/0392081 A1 | 12/2020 | Bouaboula et al. |
| 2021/0188771 A1 | 6/2021 | Rabion et al. |
| 2021/0188772 A1 | 6/2021 | Malpart et al. |

FOREIGN PATENT DOCUMENTS

| | | |
|---|---|---|
| CN | 106 924 210 | 7/2017 |
| CN | 106924210 | 7/2017 |
| EP | 1 229 036 | 8/2002 |
| WO | WO1992015579 | 9/1992 |
| WO | WO2003016270 | 2/2003 |
| WO | WO2003091239 | 11/2003 |
| WO | WO2006012135 | 2/2006 |
| WO | WO2009047343 | 4/2009 |
| WO | WO2013097773 | 7/2013 |
| WO | WO2015028409 | 3/2015 |
| WO | WO2016097072 | 6/2016 |
| WO | WO 2016/176666 | 11/2016 |
| WO | WO 2017/140669 | 8/2017 |
| WO | WO2018091153 | 5/2018 |

OTHER PUBLICATIONS

Anstead, Gregory M. et al., "2,3-Diarylindenes and 2,3-Diarylindenones: Synthesis, Molecular Structure, Photochemistry, Estrogen Receptor Binding Activity, and Comparisons with Related Triarylethylenes", J. Med.Chem., 31(7): 1316-1326 (1988).

Deroo, B.J., et al., "Estrogen Receptors and Human Disease", The Journal of Clinical Investigation, 116(3): 561-570 (2006).

Franks, et al., "Selective Estrogen Receptor Modulators: Cannabinoid Receptor Inverse Agonists with Differential CB1 and CB2 Selectively," Frontiers in Pharmacology, 7(503): 1-16 (2016).

Golub, et al., "Molecular Classification of Cancer: Class Discovery and Class Prediction by Gene Expression Monitoring", Science, 286: 531-537 (1999).

International Search Report for PCT/EP2017/053282, dated Jul. 6, 2017, 6 pages.

International Search Report for PCT/EP2017/068446, dated Sep. 12, 2017, 5 pages.

(Continued)

*Primary Examiner* — Erich A Leeser (74) *Attorney, Agent, or Firm* — Hoxie & Associates LLC (57) ABSTRACT

Herein are provided a combination of palbociclib and of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid or a pharmaceutically acceptable salt thereof, a pharmaceutical composition containing such a combination, and the therapeutic uses thereof, in particular for the treatment of cancer, including breast cancer.

11 Claims, 3 Drawing Sheets

(56) References Cited

OTHER PUBLICATIONS

International Search Report for PCT/EP2018/069901, dated Oct. 12, 2018, 3 pages.
International Search Report for PCT/EP2019/073827, dated Oct. 9, 2019, 3 pages.
International Search Report for PCT/EP2019/073823, dated Oct. 10, 2019, 3 pages.
Jordan, Craig V., "Antiestrogens and Selective Estrogen Receptor Modulators as Multifunctional Medicines. 1. Receptor Interactions," Journal of Clinical Chemistry, 46(6): 883-908 (2003).
Lala, P.K., et al., "Role of Nitric Oxide in Tumor Progression: Lessons From Experimental Tumors", Cancer and Metastasis Reviews, 17(1): 91-106 (1998).
Miller, Chris P., "SERMs: Evolutionary Chemistry, Revolutionary Biology," Current Pharmaceutical Design, 8(23): 2089-2111 (2002).
McCague, Raymond et al., "Nonisomerizable Analogues of (Z)- and (E)-4-Hydroxytamoxifen. Synthesis and Endocrinological Properties of Substituted Diphenyl Benzocycloheptene", J. Med.Chem., 31(7): 1285-1290 (1988).
Pickar, et al., "SERMs: Progress and future perspectives," Maturitas, Elsevier, 67: 129-138 (2010).
Ruff, et al., "Estrogen receptor transcription and transactivation: Structure-function relationship in DNA-and ligand-binding domains of estrogen receptors." Breast Cancer Research, 2: 353-359 (2000).
Ullrich, et al., "Estrogen receptor modulator review," Expert Opinion, 16(5):559-572 (2006).

\* cited by examiner

COMBINATION COMPRISING PALBOCICLIB AND 6-(2,4-DICHLOROPHENYL)-5-[4-[(3S)-1-(3-FLUOROPROPYL)PYRROLIDIN-3-YL]OXYPHENYL]-8,9-DIHYDRO-7H-BENZO[7]ANNULENE-2-CARBOXYLIC ACID AND ITS USE FOR THE TREATMENT OF CANCER

CROSS REFERENCE TO RELATED APPLICATIONS

This application is a U.S. National Stage application under 35 U.S.C. § 371 of International Application No. PCT/EP2018/069901, filed on Jul. 23, 2018, which claims priority to and the benefit of U.S. Provisional Application No. 62/536,121, filed on Jul. 24, 2017, and European Application No. 17305998.1, filed on Jul. 25, 2017, the contents of each of which are hereby incorporated by reference in their entireties.

Herein are provided a combination of palbociclib and of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, a pharmaceutical composition containing such a combination, and the therapeutic uses of such combination and pharmaceutical composition, in particular for the treatment of cancer.

The estrogen receptor α (ESR1) is expressed in the majority of breast tumors, enabling them to respond to the mitogenic actions of estrogens.

6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, hereafter designated as "compound (1)", is a selective estrogen receptor degrader (SERD) which has complete estrogen receptor antagonist properties and accelerates the proteasomal degradation of the estrogen receptor. This compound is disclosed in the patent application PCT/EP2017/053282, published as WO 2017/140669.

Palbociclib, also known as 6-acetyl-8-cyclopentyl-5-methyl-2-[5-(1-piperazinyl)pyridine-2-ylamino]pyrido[2,3-d]pyrimidin-7(8H)-one, is an inhibitor of cyclin-dependent kinase (CDK) 4 and 6. Palbociclib is marketed under the tradename Ibrance® and is indicated for the treatment of hormone receptor (HR)-positive, human epidermal growth factor receptor 2 (HER2)-negative locally advanced or metastatic breast cancer, in combination with an aromatase inhibitor, or in combination with fulvestrant in women who have received prior endocrine therapy. In pre- or perimenopausal women, the endocrine therapy should be combined with a luteinizing hormone-releasing hormone (LHRH) agonist.

There is always a need to find new antitumoral treatments. Now, it has been shown that a combination of compound (1) with palbociclib is well tolerated, demonstrates strong antitumor efficacy and induces tumor regression, with a synergistic effect compared to each of the active ingredient alone.

Herein is provided a combination comprising compound (1) and palbociclib.

In the combination provided herein, compound (1) may exist not only in the form of a zwitterion (i.e. a globally neutral molecule having an acid group and a basic group), but also in the form of addition salts with acids or bases. Such addition salts may be used in the above combination. Hence, herein is provided a combination comprising compound (1), or a pharmaceutically acceptable salt thereof, and palbociclib.

In an embodiment, the combination of compound (1), or a pharmaceutically acceptable salt thereof, with palbociclib shows therapeutic synergy. A combination demonstrates therapeutic synergy if its therapeutic effect is superior compared to the cumulative effect of either active agent of the combination alone.

In another embodiment, compound (1), or a pharmaceutically acceptable salt thereof, and palbociclib are administered by the oral route.

Provided herein is also a combination of compound (1), or a pharmaceutically acceptable salt thereof, and palbociclib for its use as a medicament.

Provided herein is also a pharmaceutical composition comprising compound (1), or a pharmaceutically acceptable salt thereof, and palbociclib, as well as at least one pharmaceutically acceptable excipient.

The excipients are selected from the customary excipients which are known to a person skilled in the art. More particularly, the excipients are selected from those useful for oral administration in whatever form (liquid solution, dispersion or suspension, tablets, capsules or the like).

In another embodiment, compound (1), or a pharmaceutically acceptable salt thereof, and palbociclib may be administered simultaneously, separately, or spaced out over a period of time (sequential administration). Therefore, the combination provided herein is not exclusively limited to the one which is obtained by physical association of the constituents in a single pharmaceutical composition, but also to those which allow a separate administration, which can be simultaneous or spaced out (or "spread out") over time.

Herein is also provided a pharmaceutical kit which comprises:
 (i) a first pharmaceutical composition comprising compound (1), or a pharmaceutically acceptable salt thereof, and at least one pharmaceutically acceptable excipient;
 (ii) a second pharmaceutical composition comprising palbociclib, and at least one pharmaceutically acceptable excipient;
both pharmaceutical compositions (i) and (ii) being in separate compartments and being intended to be independently administered, each administration with regards to the other one being simultaneous, separated or spread out (sequential) over time.

In the combinations, pharmaceutical compositions and pharmaceutical kit described above, the compound (1) or pharmaceutically acceptable salt thereof and palbociclib are advantageously present at effective doses, adapted considering the treated pathology and the condition of the patient to which it is administered. In particular for palbociclib, the recommended starting dose for cancer treatment for adult patients is 125 mg once daily for 21 days followed by 7 days off treatment, along with dosing interruption and/or dose reductions based on individual safety and tolerability.

Herein is also provided a combination comprising compound (1), or a pharmaceutically acceptable salt thereof, and palbociclib, as well as a pharmaceutical composition and kit as described above, for use in the treatment of cancer.

Herein is also provided compound (1) or a pharmaceutically acceptable salt thereof for use in the treatment of cancer by co-administration with palbociclib.

Herein is also provided palbociclib for use in the treatment of cancer by co-administration with compound (1) or a pharmaceutically acceptable salt thereof.

In another embodiment, the cancer is a hormone dependent cancer.

In another embodiment, the cancer is an estrogen receptor dependent cancer, particularly the cancer is an estrogen receptor a dependent cancer.

In another embodiment, the cancer is resistant to antihormonal treatment.

In another embodiment, the cancer is a cancer with wild type estrogen receptors.

In another embodiment, the cancer is a cancer with deregulated function of estrogen receptors related to, but not limited to, at least one epigenetic and genetic alteration of estrogen receptors such us mutation, amplification, splice variant.

In another embodiment, the cancer is a cancer with mutated estrogen receptors.

In another embodiment, the mutations of estrogen receptors can include, but not limited to, new or known mutations such as Leu536Arg, Tyr537Ser, Tyr537Asn, or Asp538Gly.

In another embodiment, the cancer is an estrogen-sensitive cancer.

In another embodiment, the cancer is breast cancer, more particularly an estrogen receptor positive breast cancer (ERα positive breast cancer), or a metastasis thereof, such as a cerebral metastasis.

Herein is also provided a method of treating the pathological conditions indicated above, particularly breast cancer, comprising administering to a subject in need thereof a therapeutically effective amount of compound (1), or a pharmaceutically acceptable salt thereof, and a therapeutically effective amount of palbociclib.

Herein is also provided a method of treating the pathological conditions indicated above, particularly breast cancer, comprising administering to a subject in need thereof a pharmaceutical composition as described above.

Herein is also provided a method of treating the pathological conditions indicated above, particularly breast cancer, comprising administering to a subject in need thereof a combination as described above.

Herein is also provided a method of treating the pathological conditions indicated above, particularly breast cancer, comprising co-administering to a subject in need thereof compound (1) or a pharmaceutically acceptable salt thereof and palbociclib.

Herein is also provided a method of treating the pathological conditions indicated above, particularly breast cancer, comprising co-administering to a subject in need thereof palbociclib and compound (1) or a pharmaceutically acceptable salt thereof.

In an embodiment of the methods described above, the subject is a human.

Herein is also provided a combination comprising compound (1), or a pharmaceutically acceptable salt thereof, and palbociclib for the manufacture of a medicament useful in treating the pathological conditions indicated above, particularly breast cancer.

Herein is also provided the use of compound (1), or a pharmaceutically acceptable salt thereof, in the manufacture of a medicament useful in treating the pathological conditions indicated above, particularly breast cancer, by co-administration with palbociclib.

Herein is also provided the use of palbociclib in the manufacture of a medicament useful in treating the pathological conditions indicated above, particularly breast cancer, by co-administration with compound (1) or a pharmaceutically acceptable salt thereof.

Herein is also provided an article of manufacture, a packaging, or an administration unit, comprising:
 a packaging material;
 the above defined combination, pharmaceutical composition or pharmaceutical kit; and
 a label or package insert contained within said packaging material, indicating that said combination, pharmaceutical composition or pharmaceutical kit is administered to a patient for the treatment of cancer.

The examples below show how to synthesize compound (1), and the pharmacological results obtained with compound (1), palbociclib and their combination against a breast cancer cell line xenograft in mice.

1-Synthesis of 6-(2,4-dichlorophenyl)-5-[4-[(3S)-1-(3-fluoropropyl) pyrrolidin-3-yl]oxyphenyl]-8,9-dihydro-7H-benzo[7]annulene-2-carboxylic acid

Figure 1:
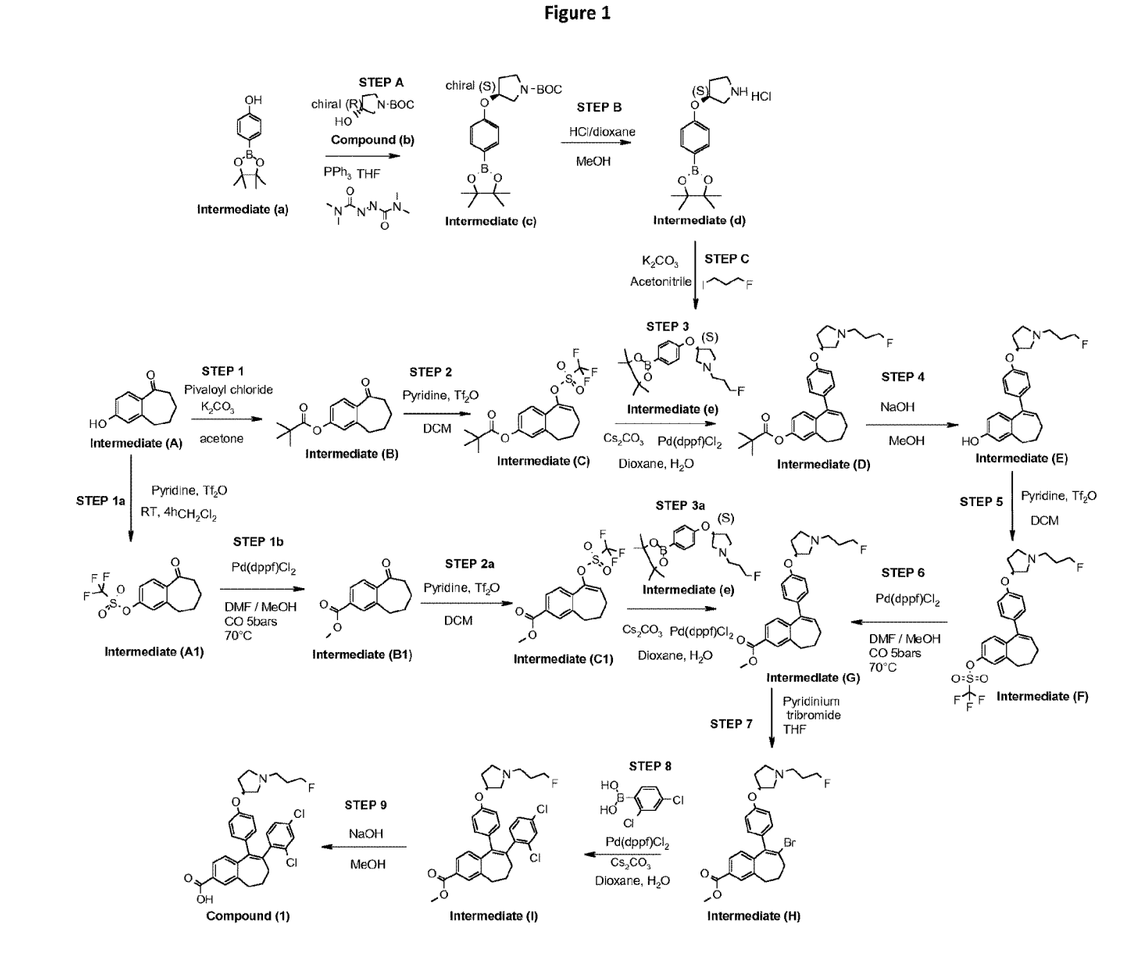
FIG. 1. Synthetic scheme for the synthesis of compound (1).

The experimental protocol for synthesizing 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid (compound (1)), described in the patent application WO 2017/140669, is reproduced below, along with its analytical data. The synthetic scheme for the synthesis of compound (1) is found in FIG. 1.

The 1H NMR spectra were performed on a Bruker Avance DRX-400 spectrometer, with the chemical shifts (6 in ppm) in the solvent dimethyl sulfoxide-d6 (d6-DMSO) referenced at 2.5 ppm at a temperature of 303 K. Coupling constants (J) are given in Hertz.

The liquid chromatography/mass spectra (LC/MS) were obtained on a UPLC Acquity Waters instrument, light scattering detector Sedere and SQD Waters mass spectrometer using UV detection DAD 210<I<400 nm and column Acquity UPLC CSH C18 1.7 µm, dimension 2.1×30 mm, mobile phase $H_2O+0.1\%$ $HCO_2H/CH_3CN+0.1\%$ $HCO_2H$.

The following abbreviations and empirical formulae are used:
AcOEt ethyl acetate
$AlCl_3$ aluminium trichloride
$Cs_2CO_3$ cesium carbonate
DCM dichloromethane
DMF N,N-dimethylformamide
DMSO dimethyl sulfoxide
HCl hydrogen chloride
$K_2CO_3$ potassium carbonate
LC/MS liquid chromatography/mass spectrometry
MeOH methanol
$MgSO_4$ magnesium sulfate
$NaHCO_3$ sodium bicarbonate
NaOH sodium hydroxyde
Pd(dppf)$Cl_2$ 1,1'bis(diphenylphosphino)ferrocene] dichloropalladium(II)
$Ph_3P$ or $P(Ph)_3$ triphenylphosphine
$Ph_3P=O$ triphenylphosphine oxide
° C. degrees Celsius
ml millilitre(s)
mmol millimole(s)
µmol micromole(s)
µM micromolar
nM nanomolar
ppm parts per million

Intermediate (c). Tert-butyl (3S)-3-[4-(4,4,5,5-tetramethyl-1,3,2-dioxaborolan-2yl)phenoxy]pyrrolidine-1-carboxylate To a solution of commercially available 4-(4,4,5,5-tetramethyl-1,3,2-dioxaborolan-2-yl)phenol (a) (82.7 g, 364.51 mmol) in THF (2 L) was added under argon (R)-1-N-Boc-3-hydroxypyrrolidine (b) (84.43 g, 437.41 mmol) followed by N,N,N',N'-tetramethylazodicarboxamide (99.1 g, 546.77 mmol). The clear reaction mixture turned orange and triphenylphosphine (143.41 g, 546.77 mmol) was added. The reaction mixture was stirred at room temperature for 24 hours, meanwhile a precipitate of triphenylphosphine oxide formed (Ph$_3$P=O). The reaction mixture was poured in water (1.5 L) and extracted with ethyl acetate (AcOEt) (3×1.5 L). Gathered organic phases were dried over magnesium sulfate (MgSO$_4$), filtered and concentrated under reduced pressure. The residue was taken up into diisopropylether (1.5 L) and the solid formed (Ph$_3$P=O) was filtered. The solvent was concentrated under reduced pressure and the residue purified by column chromatography eluting with a mixture of heptane with AcOEt (90/10; v/v) to give 145 g (100%) of tert-butyl (3S)-3-[4-(4,4,5,5-tetramethyl-1,3,2-dioxaborolan-2-yl)phenoxy]pyrrolidine-1-carboxylate (c) as a colorless oil.

$^1$H NMR (400 MHz, DMSO-d6, δ ppm): 1.27 (s: 12H); 1.39 (s: 9H); 2.05 (m: 1H); 2.14 (m: 1H); 3.37 (3H); 3.55 (m: 1H); 5.05 (s: 1H); 6.94 (d, J=8.4 Hz: 2H); 7.61 (d, J=8.4 Hz: 2H)

Intermediate (d). (3S)-3-[4-(4,4,5,5-tetramethyl-1,3,2-dioxaborolan-2yl)phenoxy]pyrrolidine, hydrochloride

To a solution of (S)-tert-butyl 3-(4-(4,4,5,5-tetramethyl-1,3,2-dioxaborolan-2-yl)phenoxy)pyrrolidine-1-carboxylate (c) (80 g, 195.23 mmol) in MeOH (450 ml) was added slowly HCl 4N in dioxane (250 ml).

After 1.5 hours, the reaction mixture was concentrated under reduced pressure and the residue was taken up into Et$_2$O with stirring to give a solid which then was filtered and dried under vacuum to give 61.8 g (95%) of (3S)-3-[4-(4,4,5,5-tetramethyl-1,3,2-dioxaborolan-2yl)phenoxy]pyrrolidine, hydrochloride (d) as a white powder.

$^1$H NMR (400 MHz, DMSO-d6, δ ppm): 1.28 (s: 12H); 2.10 (m: 1H); 2.21 (m: 1H); 3.31 (3H); 3.48 (m: 1H); 5.19 (m: 1H); 6.97 (d, J=8.4 Hz: 2H); 7.63 (d, J=8.4 Hz: 2H); 9.48 (s: 1H); 9.71 (s: 1H).

LC/MS (m/z, MH$^+$): 290

Intermediate (e). (3S)-1-(3-fluoropropyl)-3-[4-(4,4,5,5-tetramethyl-1,3,2-dioxaborolan-2-yl)phenoxy]pyrrolidine To a suspension of (S)-3-(4-(4,4,5,5-tetramethyl-1,3,2-dioxaborolan-2-yl)phenoxy)pyrrolidine hydrochloride (d) (20 g, 61.42 mmol) in acetonitrile (100 ml), was added K$_2$CO$_3$ (21.22 g, 153.54 mmol) and 1-iodo-3-fluoropropane (12.15 g, 61.42 mmol), under argon. The reaction mixture was stirred at 40° C. for 24 hours. After cooling to room temperature, the reaction mixture was filtered and washed with acetonitrile. The filtrate was concentrated under reduced pressure and the residue was taken up in DCM and the solid formed was filtered and washed with DCM. The filtrate was concentrated to give 21.5 g (100%) of (3S)-1-(3-fluoropropyl)-3-[4-(4,4,5,5-tetramethyl-1,3,2-dioxaborolan-2-yl)phenoxy]pyrrolidine (e) as a yellow foam.

$^1$H NMR (400 MHz, DMSO-d6, δ ppm): 1.27 (s: 12H); 1.77 (m: 2H); 1.84 (m: 1H); 2.27 (m: 1H); 2.41 (m: 1H); 2.49 (2H); 2.62 (dd, J=2.6 and 10.4 Hz: 1H); 2.69 (m: 1H); 2.83 (dd, J=6.2 and 10.4 Hz: 1H); 4.47 (td, J=6.2 and 47 Hz: 2H); 4.99 (m: 1H); 6.77 (d, J=8.4 Hz: 2H); 7.58 (d, J=8.4 Hz: 2H).

LC/MS (m/z, MH$^+$): 350

Intermediate (B). 5-oxo-6,7,8,9-tetrahydro-5H-benzo[7]annulen-2-yl 2,2-dimethylpropanoate

To a solution of 2-hydroxy-6,7,8,9-tetrahydro-5H-benzo[7]annulen-5-one (A) (1.52 g, 8.63 mmol), in acetone (60 ml), was added K$_2$CO$_3$ (1.19 g, 8.63 mmol) and pivaloyl chloride (1.06 ml, 8.63 mmol). The reaction mixture was stirred at room temperature for 16 hours, filtered and concentrated under reduced pressure. The residue was purified by flash chromatography eluting with a gradient of heptane in AcOEt (100/0 to 85/15, v/v) to give 1.55 g (69%) of 5-oxo-6,7,8,9-tetrahydro-5H-benzo[7]annulen-2-yl 2,2-dimethylpropanoate (B) as a colorless oil.

¹H NMR (400 MHz, DMSO-d6, δ ppm): 7.65 (d, 1H); 7.10-7.04 (m, 2H); 2.95 (t, 2H); 2.68 (t, 2H); 1.85-1.65 (m, 4H).

LC/MS (m/z, MH⁺): 261

Intermediate (C). 9-(trifluoromethanesulfonyloxy)-6,7-dihydro-5H-benzo[7]annulen-3-yl 2,2-dimethylpropanoate To a solution of 5-oxo-6,7,8,9-tetrahydro-5H-benzo[7]annulen-2-yl 2,2-dimethylpropanoate (B) (15 g, 57.62 mmol) in DCM (500 ml) was added dropwise under argon pyridine (7.28 ml, 86.43 mmol) and trifluoromethanesulfonic anhydride (19.58 ml, 115.24 mmol). The reaction mixture was stirred at room temperature for 2 hours and ice (200 g) was added. The phases were separated, the aqueous phase was washed with DCM and the gathered organic phases were dried over MgSO₄, filtered and evaporated under reduced pressure to give 22 g (97%) of 9-(trifluoromethanesulfonyloxy)-6,7-dihydro-5H-benzo[7]annulen-3-yl 2,2-dimethylpropanoate (C) as a white solid.

LC/MS (m/z, MH⁻): 391

Intermediate (D). 9-(4-{[(3S)-1-(3-fluoropropyl)pyrrolidin-3-yl]oxy}phenyl)-6,7-dihydro-5H-benzo[7]annulen-3-yl-2,2-dimethylpropanoate To a solution of 9-(trifluoromethanesulfonyloxy)-6,7-dihydro-5H-benzo[7]annulen-3-yl-2,2-dimethylpropanoate (C) (22 g, 56.07 mmol) and (3S)-1-(3-fluoropropyl)-3-[4-(tetramethyl-1,3,2-dioxaborolan-2-yl)phenoxy]pyrrolidine (e) (20.56 g, 58.87 mmol) in dioxane (420 ml) and water (120 ml) was added under argon Pd(dppf)Cl₂ (2.75 g, 3.36 mmol) and Cs₂O₃ (36.57 g, 112.13 mmol). The reaction mixture was stirred for 1 hour at room temperature and was partitioned between water and DCM. The aqueous phase was washed with DCM and the gathered organic phases dried over MgSO₄, filtered and concentrated under reduced pressure. The residue was purified by column chromatography eluting with a gradient of MeOH in DCM (0 to 5%; V/V) to give 31 g (100%) of 9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D).

LC/MS (m/z, MH⁺): 466

Intermediate (E). 9-(4-{[(3S)-1-(3-fluoropropyl)pyrrolidin-3-yl]oxy}phenyl)-6,7-dihydro-5H-benzo[7]annulen-3-ol To a solution under argon of 9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D) (24.8 g, 53.26 mmol) in MeOH (300 ml), was added NaOH 5M (23 ml, 115.00 mmol). The reaction mixture was stirred for 2 hours at room temperature. pH was then adjusted to 7 by addition of 6N aqueous HCl solution. The MeOH was concentrated under reduced pressure, then DCM was added. The organic phase was dried over MgSO₄, and concentrated under reduced pressure. The residue was purified by flash chromatography eluting with a gradient of DCM/MeOH from 100/0 to 95/05 to give 18.8 g (93%) of 9-(4-{[(3S)-1-(3-fluoropropyl)pyrrolidin-3-yl]oxy}phenyl)-6,7-dihydro-5H-benzo[7]annulen-3-ol (E) as a beige solid.

LC/MS (m/z, MH⁺): 382

Intermediate (F). 9-(4-{[(3S)-1-(3-fluoropropyl) pyrrolidin-3-yl]oxy}phenyl)-6,7-dihydro-5H-benzo[7]annulen-3-yl trifluoromethanesulfonate

To a solution of 9-(4-{[(3S)-1-(3-fluoropropyl)pyrrolidin-3-yl]oxy}phenyl)-6,7-dihydro-5H-benzo[7]annulen-3-ol (E) (20.6 g, 54.00 mmol) in DCM (200 ml) and pyridine (6.55 ml, 81.00 mmol), cooled to 5° C. (ice bath), was added dropwise trifluoromethanesulfonic anhydride (18.93 ml, 108.00 mmol) under argon, and the reaction temperature was maintained <15° C. The ice bath was removed, and the brown suspension was stirred at room temperature for 2 hours. Ice (200 g) and DCM (200 ml) were added and the phases separated. The organic phase was dried over MgSO$_4$, and concentrated under reduced pressure. The residue was purified by flash chromatography eluting with a gradient of DCM/MeOH from 100/0 to 95/05 to give 24.7 g (89.1%) of 9-(4-{[(3S)-1-(3-fluoropropyl)pyrrolidin-3-yl]oxy}phenyl)-6,7-dihydro-5H-benzo[7]annulen-3-yl trifluoromethanesulfonate (F) as a brown oil.
LC/MS (m/z, MH$^+$): 514

Intermediate (G). Methyl 9-(4-{[(3S)-1-(3-fluoropropyl)pyrrolidin-3-yl]oxy}phenyl)-6,7-dihydro-5H-benzo[7]annulene-3-carboxylate To a solution of 9-(4-{[(3S)-1-(3-fluoropropyl)pyrrolidin-3-yl]oxy}phenyl)-6,7-dihydro-5H-benzo[7]annulen-3-yl trifluoromethanesulfonate (F) (10.1 g, 19.67 mmol) in DMF (66 ml) and MeOH (33 ml), were added Pd(dppf)Cl$_2$ (909 mg, 1.18 mmol) and diisopropylethylamine (7.21 ml). The black suspension was carbonylated in an autoclave at 70° C. under 5 bars of CO for 5 hours. The reaction mixture was filtered, then the filtrate was partially concentrated under reduced pressure. The residue was partitioned between AcOEt and water. The organic phase was washed with water (2×100 ml), dried over MgSO$_4$, and concentrated under reduced pressure. The residue was purified by flash chromatography eluting with a gradient of DCM/MeOH from 100/0 to 95/05 to give 7.13 g (86%) of methyl 9-(4-{[(3S)-1-(3-fluoropropyl)pyrrolidin-3-yl]oxy}phenyl)-6,7-dihydro-5H-benzo[7]annulene-3-carboxylate (G) as a brown gum.
LC/MS (m/z, MH$^+$): 424

Intermediate (A1). 5-oxo-6,7,8,9-tetrahydro-5H-benzo[7]annulen-2-yltrifluoromethanesulfonate To a solution of commercially available 2-hydroxy-6,7,8,9-tetrahydro-5H-benzo[7]annulen-5-one (A) (18.5 g, 105 mmol) in DCM (185 ml) and lutidine (13.35 ml, 113.505 mmol), cooled at 5° C. under argon, was added dropwise trifluoromethanesulfonic anhydride (20.22 ml, 123.29 mmol) while keeping temperature between 10 and 20° C. The reaction mixture was stirred for 1 hour at 5° C. then at room temperature for 1 hour.

Then, ice (200 g) was added and the slurry partitioned between water and DCM. The organic phase was washed with aqueous NaHCO$_3$ solution, dried over MgSO$_4$, filtered off and concentrated under reduced pressure. The residue was purified by flash chromatography eluting with a gradient of heptane/AcOEt from 100 to 90/10 to give 28.2 g (87%) of 5-oxo-6,7,8,9-tetrahydro-5H-benzo[7]annulen-2-yl trifluoromethanesulfonate (A1) as an orange oil.
LC/MS (m/z, MH$^+$): 309

Intermediate (B1). Methyl 5-oxo-6,7,8,9-tetrahydro-5H-benzo[7]annulene-2-carboxylate To a solution of 5-oxo-6,7,8,9-tetrahydro-5H-benzo[7]annulen-2-yl trifluoromethanesulfonate (A1) (5.03 g, 16.32 mmol) in DMF (24 ml) and MeOH (12 ml), were added Pd(dppf)Cl$_2$ (754 mg, 0.98 mmol) and diisopropylethylamine (6 ml). The black suspension was carbonylated in an autoclave at 70° C. under 5 bars of CO for 2.5 hours. The reaction mixture was filtered, then the filtrate was partially concentrated under reduced pressure, and the residue, was partitioned between AcOEt and water. The organic phase was washed with water (2×75 ml) and aqueous HCl 0.5 N, dried over MgSO$_4$ and concentrated under reduced pressure. The residue was purified by flash chromatography eluting with a gradient of heptane/AcOEt from 100/0 to 90/10 to give 3.4 g (95%) of methyl 5-oxo-6,7,8,9-tetrahydro-5H-benzo[7]annulene-2-carboxylate (B1) as a colorless oil.

LC/MS (m/z, MH$^+$): 219

Intermediate (C1). Methyl 9-(trifluoromethanesulfonyloxy)-6,7-dihydro-5H-benzo[7]annulene-3-carboxylate To a solution of methyl 5-oxo-6,7,8,9-tetrahydro-5H-benzo[7]annulene-2-carboxylate (B1) (18.19 g, 83.34 mmol) in DCM (500 ml) and anhydrous pyridine (11 ml, 130.56 mmol), cooled at 5° C. under argon, was added dropwise trifluoromethanesulfonic anhydride (30 ml, 176.54 mmol). The reaction mixture, a thick suspension, was stirred at room temperature for 24 hours, then ice was added and partitioned between water and DCM. The organic phase was dried over MgSO$_4$, filtered off and concentrated under reduced pressure to give 29 g (100%) of methyl 9-(trifluoromethanesulfonyloxy)-6,7-dihydro-5H-benzo[7]annulene-3-carboxylate (C1) as a yellow gum.

LC/MS (m/z, MH$^+$): 351

Intermediate (G). Methyl 9-(4-{[(3S)-1-(3-fluoropropyl)pyrrolidin-3-yl]oxy}phenyl)-6,7-dihydro-5H-benzo[7]annulene-3-carboxylate To a solution of methyl 9-(trifluoromethanesulfonyloxy)-6,7-dihydro-5H-benzo[7]annulene-3-carboxylate (C1) (29 g, 82.9 mmol), (3S)-1-(3-fluoropropyl)-3-[4-(tetramethyl-1,3,2-dioxaborolan-2-yl)phenoxy]pyrrolidine (e) (28.9 g, 82.9 mmol), in dioxane (225 ml) were added Pd(dppf)Cl$_2$ under argon, complex with DCM (3.73 g, 4.57 mmol) and Cs$_2$CO$_3$ 1.5M aqueous solution (111.12 ml, 166.68 mmol). The reaction mixture was stirred at 60° C. for 1 hour.

After cooling to room temperature, the reaction mixture was poured into a mixture of water (500 ml) and AcOEt (400 ml). The organic phase was washed with brine, dried over MgSO$_4$, filtered on celite and concentrated under reduced pressure. The residue was purified by flash chromatography eluting with a gradient of DCM/MeOH from 100/0 to 95/05 to give 23 g (65%) of methyl 9-(4-{[(3S)-1-(3-fluoropropyl)pyrrolidin-3-yl]oxy}phenyl)-6,7-dihydro-5H-benzo[7]annulene-3-carboxylate (G) as a brown gum.

LC/MS (m/z, MH$^+$): 424

Intermediate (H). Methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide To a solution of methyl 9-(4-{[(3S)-1-(3-fluoropropyl)pyrrolidin-3-yl]oxy}phenyl)-6,7-dihydro-5H-benzo[7]annulene-3-carboxylate (G) (13.93 g, 32.89 mmol), in DCM (150 ml) was added under argon pyridinium tribromide (15.78 g, 44.41 mmol). The reaction mixture was stirred for 1 hour at room temperature. Water (200 ml) was added, organic phase was then dried over MgSO$_4$, and concentrated under reduced pressure. The residue was purified by flash chromatography eluting with a gradient of DCM/MeOH from 100/0 to 95/05 to give 16.4 g (85%) of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (H) as a yellow meringue.

LC/MS (m/z, MH$^+$): 502

Intermediate (I). 6-(2,4-dichloro-phenyl)-5-{4-[1-(3-fluoro-propyl)-pyrrolidin-3-yloxy]-phenyl}-8,9-dihydro-7H-benzocycloheptene-2-carboxylic acid methyl ester To a solution of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (H) (150 mg, 298.56 µmol), in dioxane (12 ml) and water (2 ml), was added 2,4-dichlorophenyl-boronic acid (62.67 mg, 328.41 µmol), $Cs_2CO_3$ (204.48 mg, 626.97 µmol), and $Pd(dppf)Cl_2$ (14.63 mg, 17.91 µmol). The reaction mixture was heated at 90° C. for 3 hours, and partitioned between AcOEt and water. The phases were separated and the organic phase washed with brine, dried over $MgSO_4$ and concentrated under reduced pressure. The residue was purified by column chromatography eluting with a mixture of DCM, acetonitrile and MeOH (96/2/2; V/V/V) to give 80 mg (47%) of 6-(2,4-dichloro-phenyl)-5-{4-[1-(3-fluoro-propyl)-pyrrolidin-3-yloxy]-phenyl}-8,9-dihydro-7H-benzocycloheptene-2-carboxylic acid methyl ester (I).

LC/MS (m/z, MH$^+$): 568

Compound (1). 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid To a solution of 6-(2,4-dichloro-phenyl)-5-{4-[1-(3-fluoro-propyl)-pyrrolidin-3-yloxy]-phenyl}-8,9-dihydro-7H-benzocycloheptene-2-carboxylic acid methyl ester (I) (80 mg, 140.72 µmol) in MeOH (5 ml) was added a solution of NaOH (562.88 µl, 5 M) and the reaction mixture was heated at 60° C. for 5 hours and the solvent removed under reduced pressure. The residue was taken up in water (10 ml) and aqueous HCl (5 M) added to pH 7. The slurry was extracted with DCM, dried over $MgSO_4$ and concentrated under reduced pressure. The solid was purified by column chromatography eluting with a mixture of DCM, acetonitrile and MeOH (90/5/5; V/V/V) to give 60 mg (77%) of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid.

$^1$H NMR (400 MHz, DMSO-d6, δ ppm): 1.68 (m, 1H); 1.79 (dm, J=25.3 Hz, 2H); 2.07 to 2.23 (m, 5H); 2.38 (m, 1H); 2.46 (t, J=7.2 Hz, 2H); 2.52 (m, 1H); 2.62 (m, 1H); 2.55 to 2.89 (m, 3H); 4.47 (td, J=6.2 and 47.6 Hz, 2H); 4.72 (m, 1H); 6.63 (d, J=8.9 Hz, 2H); 6.71 (m, 3H); 7.18 (d, J=8.4 Hz, 1H); 8.26 (dd, J=2.0 and 8.4 Hz, 1H); 7.58 (d, J=2.0 Hz, 1H); 7.63 (d, J=8.4 Hz, 1H); 7.79 (s, 1H); 12.3 (m, 1H)

LC/MS (m/z, MH+): 554

2—Evaluation of the Efficacy of 6-(2,4-dichlorophenyl)-5-[4-[(3S)-1-(3-fluoropropyl) pyrrolidin-3-yl]oxyphenyl]-8,9-dihydro-7H-benzo[7]annulene-2-carboxylic Acid Combined with Palbociclib Against a Subcutaneous Breast Cancer Cell Line Xenograft in Female Nude Mice In the present study, the anti-tumor efficacy of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid ("compound (1)"), combined with the cyclin-dependent kinase 4 (CDK4) inhibitor palbociclib, was investigated after 30 days treatment against a subcutaneous MCF7-Y537S human breast cancer cell line xenograft in female nude mice.

The treated groups included compound (1) at 5 mg/kg alone, palbociclib at 100 mg/kg alone, and the combination of compound (1) and palbociclib at the same dose and regime.

Compound (1) was orally dosed twice a day (BID) and palbociclib was orally dosed once a day (QD) for 30 days. Anti-tumor efficacy was evaluated by tumor volume measurement.

2-1: Experimental Procedure
2-1-1: Animals, Cell Line, Compounds

Female athymic nude mice were obtained from Harlan (Indianapolis, Ind., USA). Animals were allowed to acclimate for at least four days before the study enrollment. Mice were 12 to 13 weeks old and weighed between 20.2 and 27.3 grams at the beginning of the treatments. These animals were housed under conditions outlined in the NIH Guide for Care and Use of Laboratory Animals in compliance with the USDA Laboratory Animal Welfare Act.

Parental MCF7 cells were obtained from the American Type Culture Collection (ATCC® HTB-22™). MCF7-Y537S (ESR1) cell line was MCF7 cells expressing the ER.Y537S variant that was generated by Sanofi Biology Discovery Group. Y537S mutation was introduced in ESR1 construct (GenBank NM_000125.3) by site directed mutagenesis (Toy W. et al., Cancer Discovery, 2017, 7, 277-287). The construct was transfected in MCF7 cells which were selected for their growth in absence of estradiol. MCF-Y537S is an ESR1 mutation that confers estrogen-independent activity to ERα (Estrogen Receptor alpha) and contributes to endocrine resistant disease (Robinson D. R. et al., Nat Genet., 2013, 45 (12), 1446-1451). The cells were grown in Eagle's Minimum Essential Medium (EMEM) supplemented with 10% fetal bovine serum (FBS), human Insulin, in 5% $CO_2$ at 37° C. The cells were harvested in 0.25% Trypsin EDTA and washed by Dulbecco's Phosphate Buffered Saline (DPBS) and re-suspended in DPBS with 50% matrigel (Becton Dickinson catalog No. 356234, lot No. 32277). The cells ($20 \times 10^6$ cells/per mouse) were subcutaneously (SC) implanted into the right flank of female nude mice.

When the MCF7-Y537S tumors were established, the tumors were reserved as tumor stocks for fragment implantation. The tumors were serially propagated through fragment tissue transplantation subcutaneously. The fragment tumor tissues were subcutaneously implanted into the right flank of female nude mice. 50 mice were assigned in this experiment.

Compound (1) and palbociclib (commercially available, marketed under the tradename Ibrance®) were formulated as follows:

Vehicle A: 20% Labrasol® (supplied from Gattefosse SAS, France);

Vehicle B: 5% Dextrose.

Compound (1) was prepared in Vehicle A, then Solutol HS15 (purchased from Sigma) was added to the final concentration 5%, and the solution was left under stirring for an hour for complete dissolution. After that, vehicle B was added. The final pH was 5.5.

Dose volume for compound (1) administration: 10 ml/kg by oral gavage.

Doses: 5 mg/kg (dosage of compound (1) in the above volume).

Palbociclib was prepared in Vehicle A, then Solutol HS15 was added to the final concentration 5%, and the solution was left under stirring for an hour for complete dissolution. After that, vehicle B was added. The final pH was 5.5.

Dose volume: 10 ml/kg by oral gavage.

Doses: 100 mg/kg (dosage of palbociclib in the above volume).

2-1-2: Study Design, End Points

The animals required for experiment (plus extra) were pooled and implanted with MCF7-Y537S tumor fragment tissues on day 0. On day 21 post implantation, the mice were pooled and randomly distributed to the treatment and control groups (10 mice per group), where median tumor volumes for each group ranged from 202.5 to 211.5 mm³. Treatments of compound (1) and palbociclib were initiated on day 22. Compound (1) was orally administered at 5 mg/kg BID (at least 5 hours apart) and palbociclib was orally administered at 100 mg/kg QD, for 30 days. Animal body weight was assessed daily.

The dosages are expressed in mg/kg and based on daily body weight per animal. Vehicle treated animals were used as controls. Mice were checked daily and adverse clinical reactions noted. Individual mice were weighed daily until the end of the experiment. Mice would be euthanized when morbid or weight loss ≥20% was observed. Tumors were measured with a caliper twice weekly until final sacrifice. When a tumor size reached approximately 2000 mm³ or when there are animal health issues (40% area of a tumor ulcerated), animals would be euthanized and date of death recorded. Solid tumor volumes were estimated from two dimensional tumor measurements and calculated according to the following equation:

$$\text{Tumor volume (mm}^3\text{)} = \frac{\text{length (mm)} \times \text{width}^2 \text{ (mm}^2\text{)}}{2}$$

Toxicity End Points:

A dosage producing either 15% body weight loss during 3 consecutive days for an individual mouse, 20% body weight loss during 1 day, or 10% or more drug related deaths, was considered an excessively toxic dosage, unless under certain circumstances bodyweight loss or animal death can be considered non-drug related. Examples include animal handling issues such as misgavage, tumor model related issues such as tumor induced cachexia leading to body weight loss that can be observed in control or vehicle treated groups and excessive tumor ulceration. Mice that have non-drug related death or significant bodyweight loss will not be considered toxic and will be excluded from statistical analysis. Animal body weight included the tumor weight.

Efficacy End Points:

The primary efficacy end points include tumor volume changes from baseline summarized by the ratio of medians of tumor volume changes from baseline between the treated and control groups ($\Delta T/\Delta C$). Changes in tumor volume for each treated (T) and control (C) group are calculated for each animal on each day by subtracting the tumor volume on the day of first treatment (staging day) from the tumor volume on the specified observation day. The median $\Delta T$ is calculated for the treated group and the median $\Delta C$ is calculated for the control group. The ratio $\Delta T/\Delta C$ is calculated and expressed as percentage:

$$\Delta T/\Delta C = \left(\frac{\text{Median } deltaT}{\text{Median } deltaC}\right) \times 100$$

$\Delta T/\Delta C \leq 40\%$ is considered as therapeutically active, $\Delta T/\Delta C = 0\%$ is considered as tumor stasis, and $\Delta T/\Delta C < 0\%$ is considered as tumor regression (very active). $\Delta T/\Delta C > 40\%$ is considered as therapeutically inactive.

Percent tumor regression is defined as % (percentage) of tumor volume decrease in the treated group on a specified observation day compared to its volume when the study was initiated. At a specific time point (t) and for each animal, the regression percentage is calculated using the following formula:

$$\% \text{ regression (at } t) = \left(\frac{\text{volume}_{t0} - \text{volume}_{t}}{\text{volume}_{t0}}\right) \times 100$$

The median percent regression for a group on a given day is then calculated by taking the median of individual % regression values calculated for each animal in the group. The day of calculation is determined by the day when $\Delta T/\Delta C$ is calculated, excepted if median percent regression is not representative of the activity of the group. In this case, the day is determined by the first day when the median percent regression is maximal.

2-1-3: Statistical Analysis

A two-way Anova-Type analysis with factors treatment and day (repeated) is performed on tumor volume changes from baseline. It is followed by contrast analyses with Bonferroni-Holm correction for multiplicity to compare all treated groups to the control group and to compare the combination versus each single agent at the dose involved in the combination at each day from day 27 to 51.

In the figures, the medians and Median Absolute Deviation (MAD) of each group are represented for each day of measurement.

In the tables, the medians and Normalized MAD (nMAD=1.4826*MAD) of each group are reported for each day of measurement.

Tumor volume changes from baseline are calculated for each animal and each day by subtracting the tumor volume on the day of first treatment (day 21) from the tumor volume on the specified observation day.

All statistical analyses were performed using SAS version 9.2 software. A probability of less than 5% (p<0.05) was considered as significant.

2-2: Results

Compound (1) at 5 mg/kg BID, palbociclib 100 mg/kg QD and the combination of compound (1) and palbociclib at the doses and regime for 30 days were well tolerated in this study showing average body weight change in % per group at nadir (the lowest of body weight drop in the group) of −1.7% (day 22), −2.0% (day 22) and −6.4% (day 26), respectively (Table 1).

Figure 2:
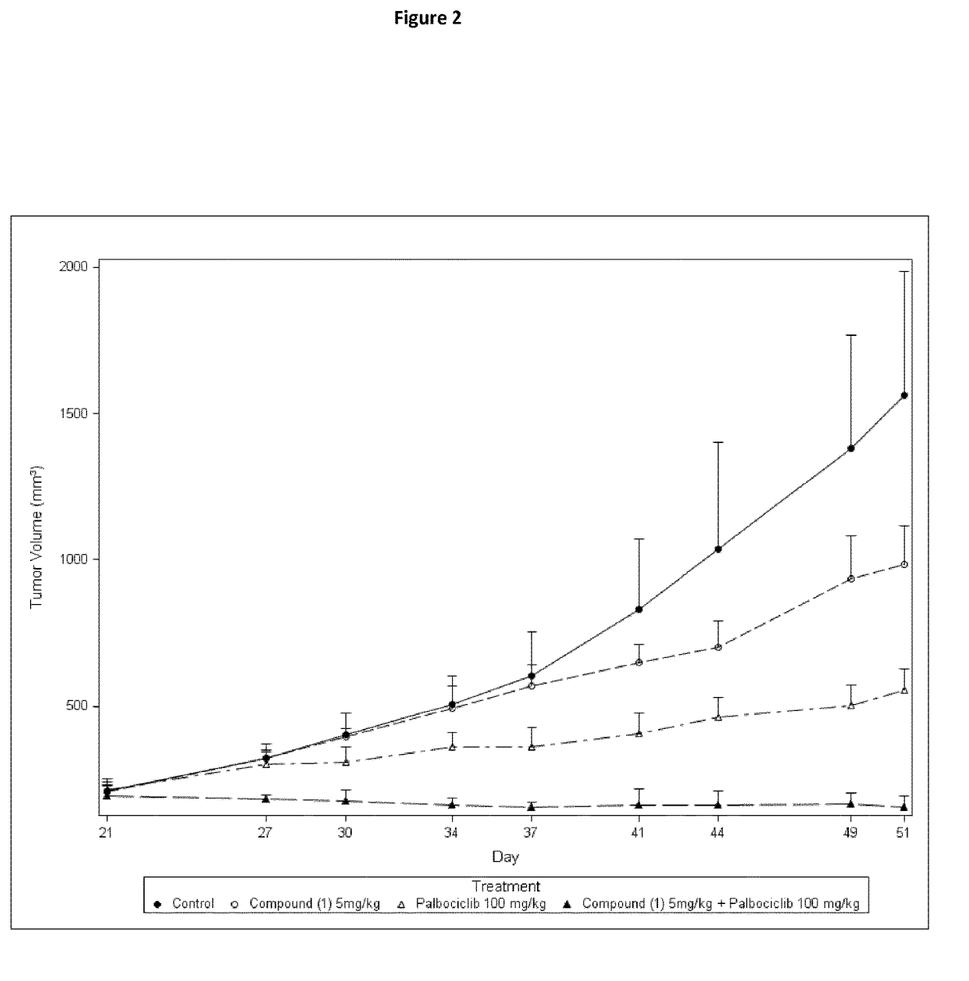
FIG. 2. Antitumor activity of compound (1) combined with palbociclib against subcutaneous human breast cancer cell line MCF7-Y537S xenograft in nude mice, showing tumor volume evolution (tumor volume in mm$^3$ versus days of treatment).
Figure 3:
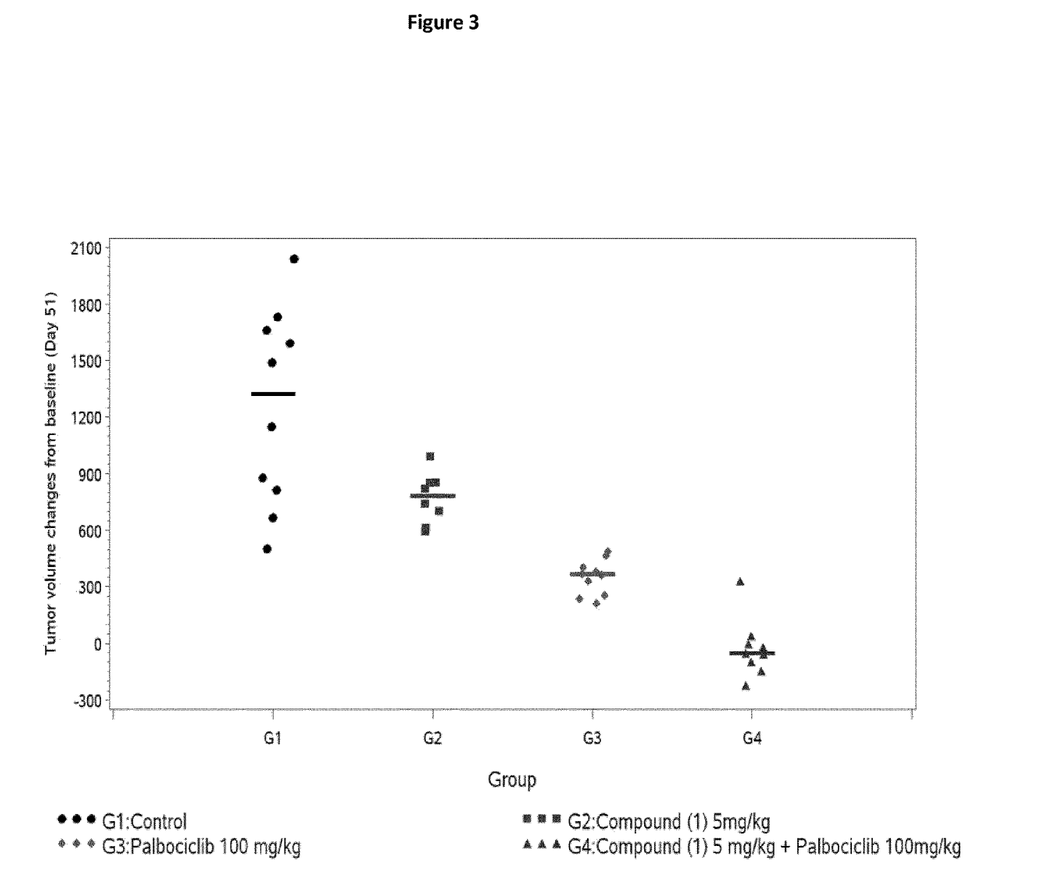
FIG. 3. Antitumor activity of compound (1) combined with palbociclib against subcutaneous human breast cancer cell line MCF7-Y537S xenograft in nude mice, showing tumor volume changes from baseline on day 51 of treatment.

Compound (1) at a dose of 5 mg/kg BID for 30 days had minimal effect on tumor growth with ΔT/ΔC value of 59% (p=0.4113) on day 51. Palbociclib at a dose of 100 mg/kg QD for 30 days achieved anti-tumor efficacy with ΔT/ΔC value of 27% (p<0.0001) on day 51. When compound (1) at 5 mg/kg combined with palbociclib 100 mg/kg with the same dose regime as BID for compound (1) and QD for palbociclib, the combination treatment demonstrated strong anti-tumor efficacy with ΔT/ΔC value less than 0 (p<0.0001) and induced tumor regression (median tumor regression 32%) on day 51. The statistical analysis indicated the combination effect was significantly different when compared to either compound (1) alone or palbociclib alone on day 51 (p<0.0001). Detailed results are shown in Tables 1, 2 and 3 below, as well as in FIGS. 2 and 3:

FIG. 2: Antitumor activity of compound (1) combined with palbociclib against subcutaneous human breast cancer cell line MCF7-Y537S xenograft in nude mice: tumor volume evolution. The curves represent medians + or − MAD (Median Absolute Deviation) at each day for each group;

FIG. 3: Antitumor activity of compound (1) combined with palbociclib against subcutaneous human breast cancer cell line MCF7-Y537S xenograft in nude mice: tumor volume changes from baseline on day 51. Points represent individual tumor volume changes from baseline on day 51, bars correspond to medians.

From this experiment, we conclude that the compound (1) at 5 mg/kg twice a day combined with the CDK4 inhibitor palbociclib at 100 mg/kg once a day induced significant anti-tumor efficacy and tumor regression in MCF7-Y537S human breast cancer cell line xenograft model in nude mice that was superior to single agents alone.

TABLE 1

Efficacy of compound (1) combined with palbociclib against subcutaneous MCF7-Y537S human breast cancer xenograft in nude mice.

| Agent | Route/ Dosage (in mL/kg per injection) | Dosage in mg/kg per injection (total dose) | Schedule in days (total of 30 days) | *Unscheduled death (total of death) | Average body weight change in % per group at nadir (day of nadir) | ΔT/ΔC in % at day 51 | Median % of regressions on day 51 | Regressions Partial | Regressions Complete | p-value on day 47[#] | Biological Interpretation |
|---|---|---|---|---|---|---|---|---|---|---|---|
| Vehicle | PO, BID (10) | — | — | 0/10 | −2.2 (22) | 100 | — | 0/10 | 0/10 | — | — |
| Compound (1) | PO, BID (10) | 5(295)[N.B.] | 22 to 51 | 2/10 | −1.7 (22) | 59 | NR | 0/8 | 0/8 | p = 0.4113 | Inactive |
| Palbociclib | PO, QD (10) | 100 (3000) | 22 to 51 | 0/10 | −2.0 (22) | 27 | NR | 0/10 | 0/10 | p <0.0001 | Active |
| Compound (1) + Palbociclib | PO, BID (10) + PO, QD (10) | 5 (295)[N.B.] + 100 (3000) | 22 to 51 | 1/10 | −2.3 (26) | <0 | 32 | 2/9 | 0/9 | p <0.0001 | Very active |

PO: per os
[N.B.] animals accepted one dose in the starting date.
NR: no regression (0% regression).
[#]Statistical analysis: Comparison of each single agent and combination versus the control group. The p-values were obtained using a contrast analysis to compare each treated group versus control at each day using Bonferroni-Holm adjustment for multiplicity after a two-way Anova-Type with repeated measures on tumor volume changes from baseline. A probability less than 5% (p <0.05) was considered as significant.
*3 mice were excluded from statistical analysis because those mice corresponded to non-drug related death or terminations during the study.

TABLE 2

Efficacy of compound (1) combined with palbociclib against subcutaneous human breast cancer cell line MCF7-Y537S xenograft model in nude mice. Comparison of each group to the control group at each day. Tumor volume changes from baseline mm$^3$: Median (nMAD)*, n and p-value[#]

| Treatment Group | Global | Day 27 | Day 30 | Day 34 | Day 37 | Day 41 | Day 44 | Day 49 | Day 51 |
|---|---|---|---|---|---|---|---|---|---|
| Control | — | 111.5 (44.48) n = 10 | 181.0 (78.58) n = 10 | 296.0 (133.43) n = 10 | 392.0 (235.73) n = 10 | 663.0 (363.24) n = 10 | 867.0 (456.64) n = 10 | 1140.0 (615.28) n = 10 | 1322.0 (633.07) n = 10 |

TABLE 2-continued

Efficacy of compound (1) combined with palbociclib against subcutaneous
human breast cancer cell line MCF7-Y537S xenograft model in nude mice.
Comparison of each group to the control group at each day.
Tumor volume changes from baseline mm$^3$: Median (nMAD)*, n and p-value#

| Treatment Group | Global | Day 27 | Day 30 | Day 34 | Day 37 | Day 41 | Day 44 | Day 49 | Day 51 |
|---|---|---|---|---|---|---|---|---|---|
| Compound (1) 5 mg/kg | — | 114.0 (19.27) n = 8 | 171.5 (31.13) n = 8 | 270.5 (112.68) n = 8 | 336.0 (112.68) n = 8 | 440.0 (39.29) n = 8 | 498.5 (91.18) n = 8 | 727.5 (160.86) n = 8 | 782.0 (112.68) n = 8 |
|  | 0.3975 | 0.6333 | 0.3909 | 0.7343 | 0.5990 | 0.2495 | 0.1950 | 0.3770 | 0.4113 |
| Palbociclib 100 mg/kg | — | 68.5 (31.88) n = 10 | 98.0 (25.20) n = 10 | 121.5 (34.10) n = 10 | 132.0 (31.88) n = 10 | 193.5 (52.63) n = 10 | 249.5 (43.74) n = 10 | 298.5 (97.11) n = 10 | 363.5 (108.23) n = 10 |
|  | <0.0001 | 0.1164 | 0.0009 | <0.0001 | <0.0001 | <0.0001 | <0.0001 | <0.0001 | <0.0001 |
| Compound (1) 5 mg/kg + Palbociclib 100 mg/kg | — | −8.0 (63.75) n = 9 | −17.0 (97.85) n = 9 | −35.0 (74.13) n = 9 | −30.0 (57.82) n = 9 | −43.0 (60.79) n = 9 | −63.0 (45.96) n = 9 | −53.0 (72.65) n = 9 | −52.0 (72.65) n = 9 |
|  | <0.0001 | 0.0077 | <0.0001 | <0.0001 | <0.0001 | <0.0001 | <0.0001 | <0.0001 | <0.0001 | p-values obtained with a contrast analysis versus control at each day with Bonferroni-Holm adjustment for multiplicity after a two-way Anova-Type on tumor volume changes from baseline.
*MAD = Median Absolute Deviation; nMAD = normalized MAD; nMAD = 1.4826*MAD.
For palbociclib at 100 mg/kg, the effect on tumor volume changes from baseline is significant compared to the control group from day 30 to day 51.
For the combination compound (1) at 5 mg/kg + palbociclib at 100 mg/kg, the effect on tumor volume changes from baseline is significant compared to the control group from day 27 to day 51.
n = number of animals. 3 mice were excluded from statistical analysis because those mice corresponded to non-drug related death or terminations during the study.

TABLE 3

Efficacy of compound (1) combined with palbociclib against subcutaneous human breast
cancer cell line MCF7-Y537S xenograft model in nude mice. Comparison of compound (1)
5 mg/kg and palbociclib 100 mg/kg as single agents versus the combination at each day.
Tumor volume changes from baseline mm$^3$: Median (nMAD)*, n and p-value#

| Treatment Group | Global | Day 27 | Day 30 | Day 34 | Day 37 | Day 41 | Day 44 | Day 49 | Day 51 |
|---|---|---|---|---|---|---|---|---|---|
| Compound (1) 5 mg/kg + Palbociclib 100 mg/kg | — | −8.0 (63.75) n = 9 | −17.0 (97.85) n = 9 | −35.0 (74.13) n = 9 | −30.0 (57.82) n = 9 | −43.0 (60.79) n = 9 | −63.0 (45.96) n = 9 | −53.0 (72.65) n = 9 | −52.0 (72.65) n = 9 |
| Palbociclib 100 mg/kg | — | 68.5 (31.88) n = 10 | 98.0 (25.20) n = 10 | 121.5 (34.10) n = 10 | 132.0 (31.88) n = 10 | 193.5 (52.63) n = 10 | 249.5 (43.74) n = 10 | 298.5 (97.11) n = 10 | 363.5 (108.23) n = 10 |
|  | <0.0001 | 0.2417 | 0.0736 | 0.0026 | 0.0002 | <0.0001 | <0.0001 | <0.0001 | <0.0001 |
| Compound (1) 5 mg/kg | — | 114.0 (19.27) n = 8 | 171.5 (31.13) n = 8 | 270.5 (112.68) n = 8 | 336.0 (112.68) n = 8 | 440.0 (39.29) n = 8 | 498.5 (91.18) n = 8 | 727.5 (160.86) n = 8 | 782.0 (112.68) n = 8 |
|  | <0.0001 | 0.0342 | <0.0001 | <0.0001 | <0.0001 | <0.0001 | <0.0001 | <0.0001 | <0.0001 | p-values obtained with a contrast analysis to compare the combinations of compound (1) and palbociclib versus each single agent at the dose involved in the combination at each day with Bonferroni-Holm adjustment for multiplicity after a two-way Anova-Type on tumor volume changes from baseline.
*MAD = Median Absolute Deviation; nMAD = normalized MAD; nMAD = 1.4826*MAD
The effect of the combination of compound (1) at 5 mg/kg + palbociclib at 100 mg/kg is significantly greater than the effect of palbociclib at 100 mg/kg alone on day 34 to day 51.
The effect of the combination of compound (1) at 5 mg/kg + palbociclib at 100 mg/kg is significantly greater than the effect of compound (1) at 5 mg/kg alone on day 27 to day 51.
n = number of animals. 3 mice were excluded from statistical analysis because those mice corresponded to non-drug related death or terminations during the study.

The invention claimed is:

1. A method of treating cancer comprising the administration to a subject in need thereof a combination of the compound 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and palbociclib.

2. The method according to claim 1, wherein the cancer is breast cancer.

3. A pharmaceutical composition comprising a combination of the compound 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and palbociclib, and at least one pharmaceutically acceptable excipient.

4. The pharmaceutical composition according to claim 3, wherein the compound and the palbociclib are present in amounts which provide therapeutic synergy.

5. The method according to claim 1, wherein the compound and the palbociclib are administered simultaneously as a single pharmaceutical composition comprising the compound, the palbociclib and at least one pharmaceutically acceptable excipient.

6. The method according to claim 1, wherein the compound and the palbociclib are administered in amounts which provide therapeutic synergy.

7. The method according to claim 1, wherein the compound and the palbociclib are administered simultaneously as separate pharmaceutical compositions.

8. The method according to claim 1, wherein the compound and the palbociclib are administered separately and spaced out over a period of time.

9. A pharmaceutical kit comprising:
   (i) a first pharmaceutical composition comprising 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and at least one pharmaceutically acceptable excipient; and
   (ii) a second pharmaceutical composition comprising palbociclib, and at least one pharmaceutically acceptable excipient;
   wherein both pharmaceutical compositions (i) and (ii) are in separate compartments.

10. The method according to claim 2, wherein the breast cancer is an estrogen-dependent breast cancer.

11. The method according to claim 2, wherein the breast cancer is an estrogen-receptor positive breast cancer, or a metastasis thereof.

* * * * *